US008329284B2

(12) United States Patent
Seitz

(10) Patent No.: US 8,329,284 B2
(45) Date of Patent: Dec. 11, 2012

(54) IDENTIFICATION DEVICE AND APPLICATION THEREOF

(76) Inventor: Peter Seitz, München (DE)

( * ) Notice: Subject to any disclaimer, the term of this patent is extended or adjusted under 35 U.S.C. 154(b) by 1928 days.

(21) Appl. No.: 10/620,549

(22) Filed: Jul. 16, 2003

(65) Prior Publication Data

US 2004/0058134 A1  Mar. 25, 2004

(30) Foreign Application Priority Data

Jul. 16, 2002 (DE) .................................. 102 32 197

(51) Int. Cl.
*B41M 5/00* (2006.01)
(52) U.S. Cl. ........... 428/195.1; 283/81; 283/78; 367/51; 235/380; 428/40.1
(58) Field of Classification Search .................. 428/40.1, 428/195.1; 283/78, 81; 367/51; 235/380; 702/138, 127; 356/601; 73/862.043, 862.381, 73/862.451, 862.68
See application file for complete search history.

(56) References Cited

U.S. PATENT DOCUMENTS

| | | | |
|---|---|---|---|
| 3,818,756 A | 6/1974 | Barron et al. | |
| 4,857,916 A | 8/1989 | Bellin | |
| 4,960,749 A * | 10/1990 | Miura et al. | 503/213 |
| 5,078,426 A * | 1/1992 | Reardon | 283/78 |
| 5,375,397 A | 12/1994 | Ferrand et al. | |
| 5,454,600 A * | 10/1995 | Floyd | 283/78 |
| 5,473,144 A * | 12/1995 | Mathurin, Jr. | 235/380 |
| 5,479,528 A | 12/1995 | Speeter | |
| 5,627,327 A * | 5/1997 | Zanakis | 73/862.042 |
| 5,885,229 A * | 3/1999 | Yamato et al. | 600/592 |
| 5,902,111 A | 5/1999 | Lindsey | |
| 6,044,717 A * | 4/2000 | Biegelsen et al. | 73/862.583 |
| 6,131,464 A * | 10/2000 | Pare et al. | 73/714 |
| 6,309,724 B1 * | 10/2001 | Kulper et al. | 428/40.1 |
| 6,331,893 B1 * | 12/2001 | Brown et al. | 356/601 |
| 6,334,363 B1 * | 1/2002 | Testud et al. | 73/862.046 |
| 6,345,839 B1 * | 2/2002 | Kuboki et al. | 280/735 |
| 6,360,598 B1 * | 3/2002 | Calame et al. | 73/172 |
| 6,684,717 B2 * | 2/2004 | Jiang et al. | 73/862.046 |

(Continued)

FOREIGN PATENT DOCUMENTS

DE  31 49 958  7/1983

(Continued)

OTHER PUBLICATIONS

"Footprint-Based Personal Recognition", Kazuki Nakajima, IEE transactions on Biomedical Engineering, vol. 47, No. 11, Nov. 2000.*

(Continued)

*Primary Examiner* — D. Lawrence Tarazano
*Assistant Examiner* — Tamra L Dicus
(74) *Attorney, Agent, or Firm* — Merchant & Gould P.C.

(57) ABSTRACT

Identification devices are known, e.g. in the form of labels to be attached by sewing or adhesive, monograms and the like, for the individualizing identification of items of clothing, shoes, shoe inserts or similar personal objects to be worn on a person's body. Whenever such identification devices are easy to read and to manufacture, they usually have relatively little recognition value. It is proposed to provide an identification device with, or to produce it in the form of, an image of a pressure-distribution pattern obtained by at least two-dimensional sampling of a pressure distribution between a part of the person's body and a substantially solid object.

6 Claims, 5 Drawing Sheets

U.S. PATENT DOCUMENTS

| | | | |
|---|---|---|---|
| 6,724,689 B2 * | 4/2004 | Koenig | 367/125 |
| 6,735,547 B1 * | 5/2004 | Yfantis | 702/155 |
| 6,752,028 B2 * | 6/2004 | Bechmann | 73/862.391 |

FOREIGN PATENT DOCUMENTS

| | | |
|---|---|---|
| DE | 100 29 854 A1 | 12/2001 |

OTHER PUBLICATIONS

"Piezo-dynamometry of foot-to-floor interactions during locomotion", Velio Macellari, 18th Annual Internation Conference of the IEE Engineering in Medicine and Biology Socieyt, Amseterdam 1996 2.6.1: Locomotion.*

"Pedography for the diabetic foot" at http://www.novel.de; "pedar-x softwar" at http://www.novel.de.*

Novel quantiy pressure distribution measurement-emed-pedar-pliance Mar. 23, 2000.*

Patent Abstracts of Japan. JP 1 178836, Jul. 17, 1989.

* cited by examiner

IDENTIFICATION DEVICE AND APPLICATION THEREOF

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to an identification device for the individualized identification of items of clothing, shoe inserts or similar objects to be worn on a person's body.

BACKGROUND OF THE INVENTION

As a result of industrial mass production it is becoming increasingly difficult to distinguish "one's own" (branded) athletics shoes from those of others who are engaged in the same sport and have chosen the same brand. The same problem arises in the case of knitwear, pants, gloves and the like.

One possible means of identifying, e.g., a textile item of clothing consists in embroidering a monogram onto it. However, this is extraordinarily laborious, and always requires close examination. Furthermore, it is very likely that different people with slightly different names will use the same monogram.

BRIEF SUMMARY OF THE INVENTION

The object of the present invention is to provide an identification device such that easy recognizability is very likely to ensured along with a high degree of individualization.

According to a first aspect of the present invention there is provided an identification device for individualizing the identification of a personal item such as clothing, shoes, shoe inserts and similar objects to be worn on a person's body, comprising an image of a pressure-distribution pattern obtained by at least one at least two-dimensional sampling of a pressure distribution between a part of a person's body and a substantially solid object.

Surprisingly, it turns out that such a "pattern", consisting of a limited number of points or area elements, firstly has an extremely high recognition value, and also is nearly as typical of the individual person as a fingerprint. Whereas a fingerprint can be distinguished from another person's fingerprint only by a specialist, it is extraordinarily easy to distinguish the pressure-distribution patterns of various people. Devices with which to implement this measurement procedure are disclosed, e.g., in the patent EP 0264047 B1 and the additional documents cited therein.

The discrimination becomes especially simple, and the individualization function especially effective, when pressures of different magnitude are represented by area elements of different colors or shadings. In contrast to a fingerprint, this representation makes available a third dimension, namely the color or shading, and humans are capable of memorizing such distributions of color or structural patterns very well and distinguishing them from other patterns.

According to a second aspect of the present invention there is provided a method of manufacturing an identification device for the individualizing identification of a personal item to be worn on a person's body, comprising the steps of
measuring a pressure-distribution pattern by an at least two-dimensional sampling of a pressure distribution between a part of the person's body and a substantially solid object;
storing the pressure-distribution pattern; and
producing an image of the pressure-distribution pattern, in which different high pressures are represented graphically.

The sampling of the pressure distribution preferably comprises a plurality of scans of various pressure distributions that occur during the course of a movement in which contact between the body part and the substantially rigid object is established and then abolished. This process can be visualized very readily, for example, by imagining the sequence of movements that occurs during walking, and the changing two-dimensional distributions of pressure under the foot that are produced during this activity. For the actual measurement it is possible, for instance, to take the means of the pressures at each measurement point over the entire course of the movement, or else to use only the peak values, and convert these to color values or different shadings that are then assembled to produce a "static" image, which can serve as the identification device.

Such an identification device, i.e. such an image, can then for example be used directly, by printing it onto an item of clothing, or a commercially available printer can be used to print it on film which is then "ironed onto" the clothing.

It is obviously useful and particularly advantageous to employ the identification device to identify a shoe or a removable insole, in which case the pressure-distribution pattern is that measured under the foot during walking. Given that the pressure-distribution pattern is very person-specific, especially in the case of dynamic processes, for instance, walking, there is no need to store the pattern so as to be able to use it again when new shoes are purchased; instead, the pattern can be produced anew each time, for example in the shoe store itself, which is particularly simple. The resulting pattern will recognizably resemble the pattern previously obtained. This pattern can be attached to the insole either as a reduced image or in the original scale, so that it covers the whole insole.

When the identification device is used to identify a pair of pants, for example, it is useful to measure the pressure distribution when the wearer sits down and stands up again or during parts of this movement sequence, or else to obtain a static pattern of the pressure distribution. This pressure-distribution pattern, in turn, as an identification device can be printed on the clothing either to scale or in any desired reduction/enlargement. The same applies to gloves, on the palm or back surface of which can be printed the pressure distribution measured when an object is grasped or the surface of the hand is pressed against an object.

In the following the invention is described by way of example with reference to the accompanying drawings.

DETAILED DESCRIPTION OF THE INVENTION

Figure 1:
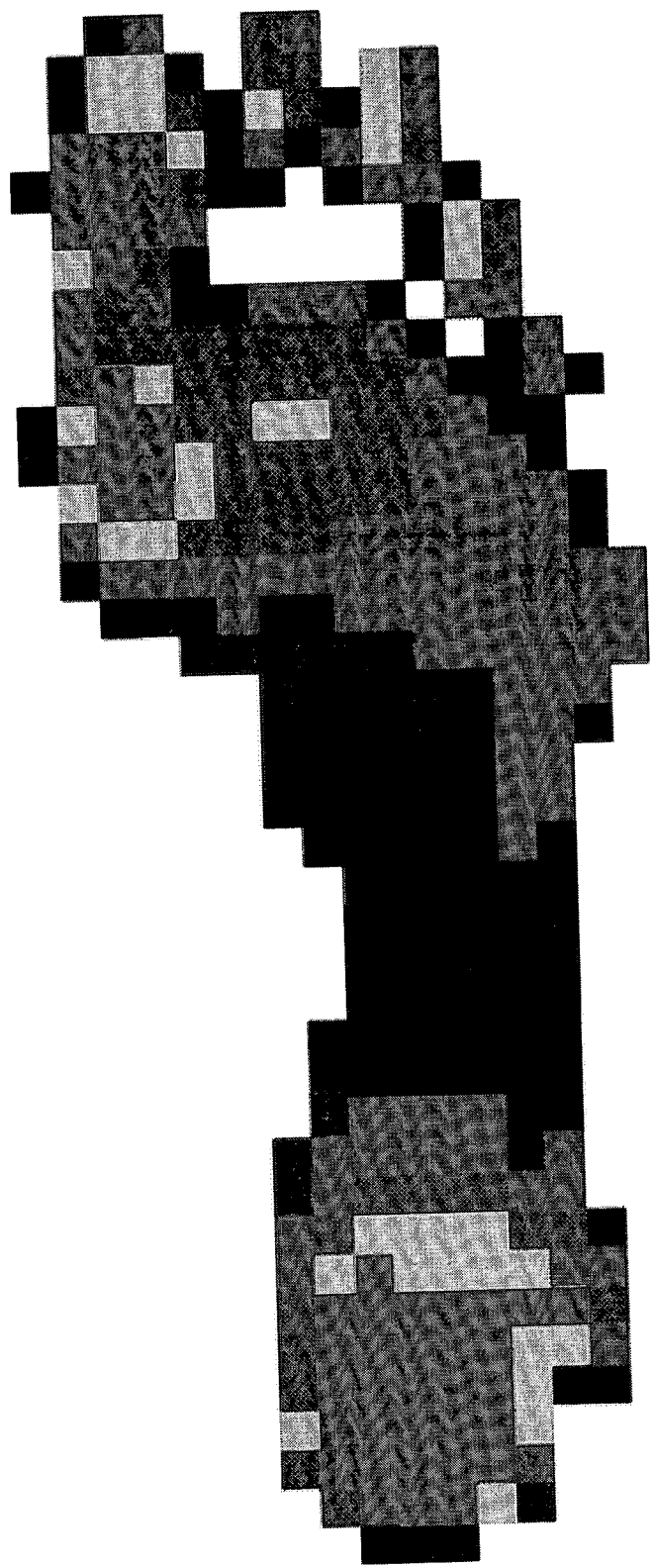
FIG. 1 shows an identification device in the form of a first "footprint" picture.
Figure 2:
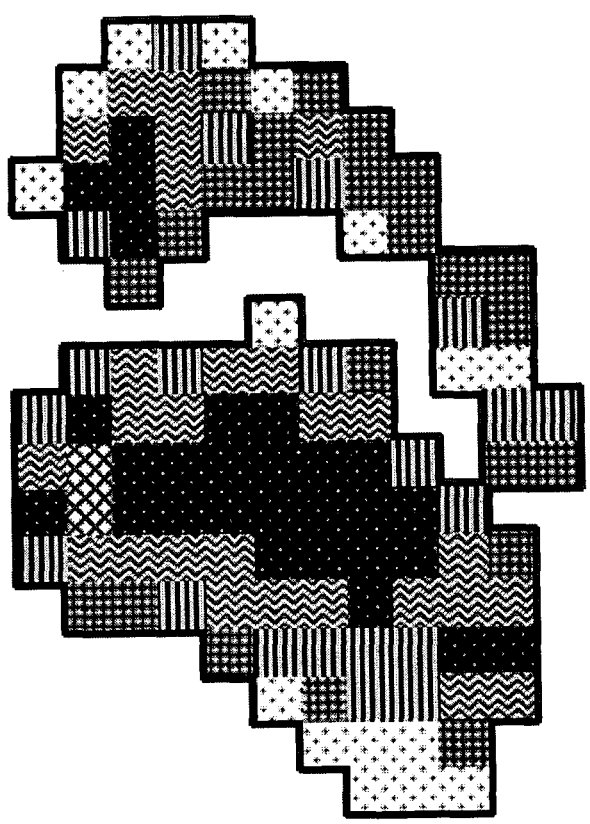
FIG. 2 shows an identification device in the form of a footprint picture of a person other than that of the picture shown in FIG. 1.
Figure 2:
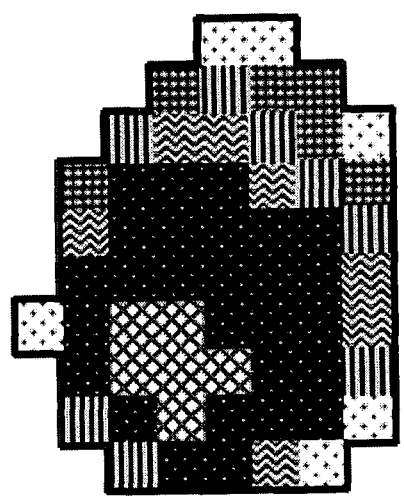

The pressure-distribution patterns shown in FIG. 1 and FIG. 2 represent peak values produced when the foot is rolled on a substrate during a stepping process. As is evident in the drawings, the two pressure-distribution patterns are very different. This is not ascribable to differences in the shapes of the feet; those differences would be much smaller and very difficult to discern. Instead, by means of the special method used here to produce the image, and hence the identification device, the individual course of movement, i.e. the "muscle-activation pattern", is also detected, so that not only the shape (as in the case of a fingerprint) but also the way in which the person "uses" the body is represented.

Figure 3:
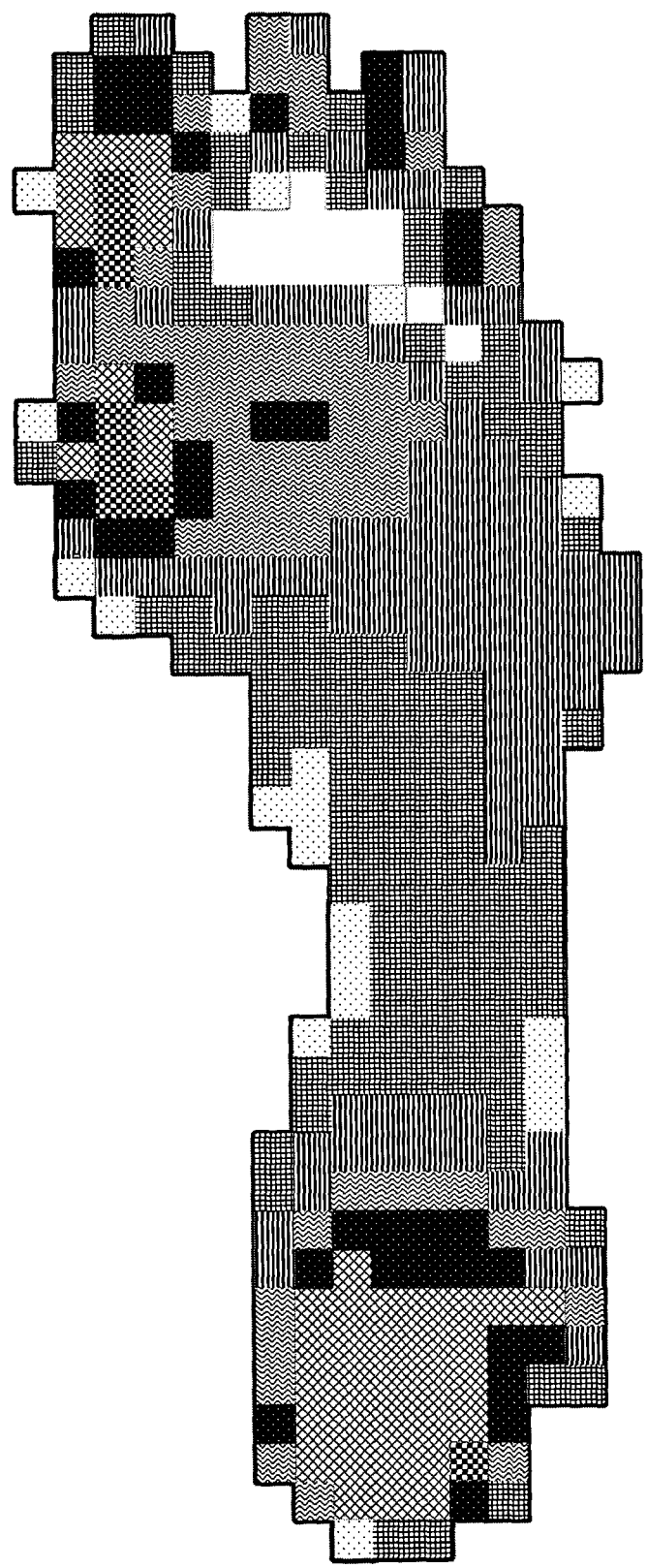
FIG. 3 shows the footprint according to FIG. 1 in another representation.

The picture shown in FIG. 3 differs from that in FIG. 1 in that instead of color values or—the only possibility for the attached figures, for technical reasons—gray values, here the measured pressures are represented by differently patterned shading. In this case, as well, the recognition value is very high.

Figure 4:
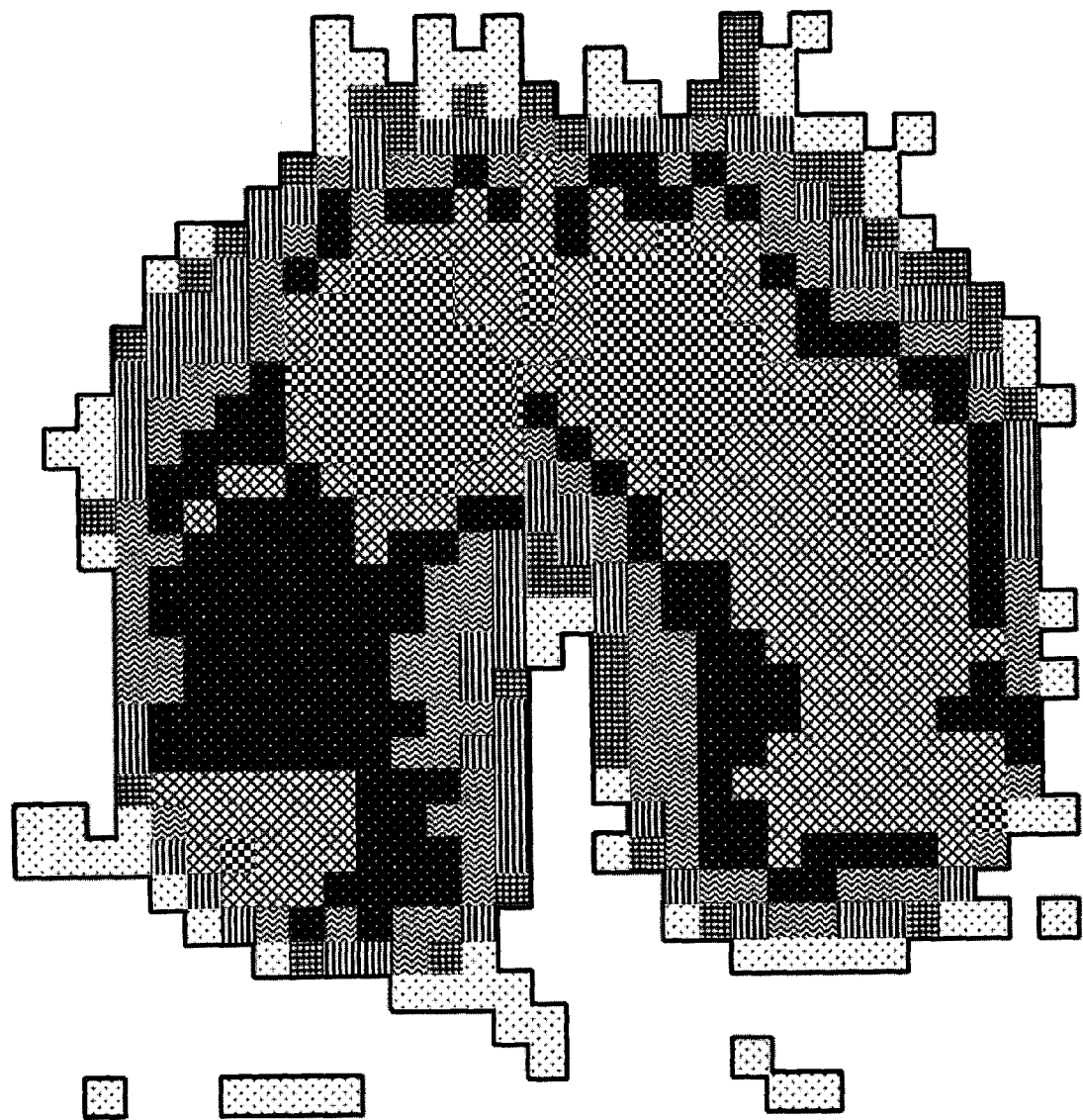
FIG. 4 shows an identification device with a sitting-surface distribution pattern.

In the picture shown in FIG. 4 the pressure distribution on the seat of a rolling chair is represented. Here, again, various people differ to an astonishing degree from one another, because again the play of the muscles, the elasticity/stiffness of the various body zones and similar factors also contribute to the image.

Figure 5:
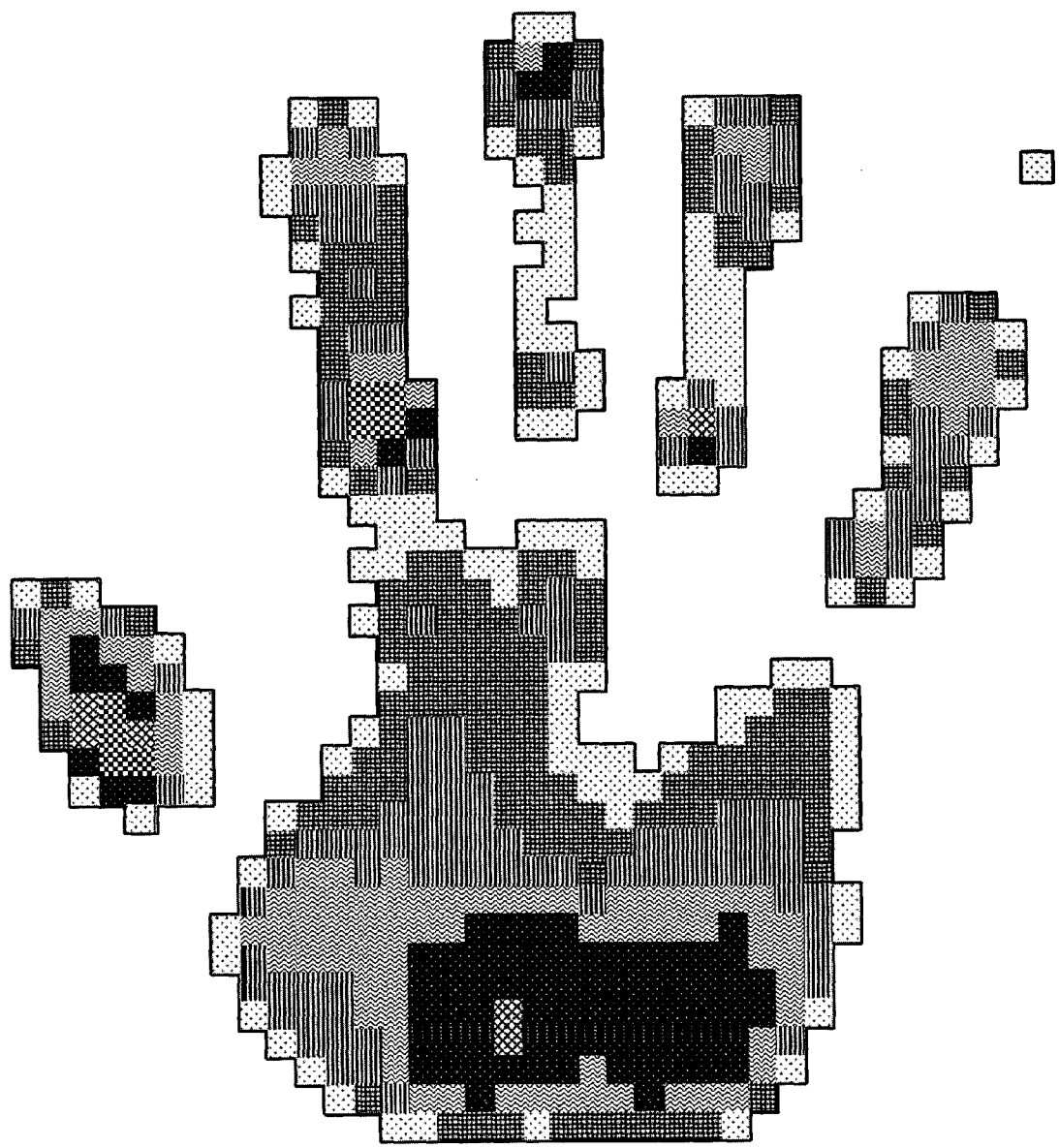
FIG. 5 shows an identification device with a hand-pressure distribution.

In FIG. 5 the pressure distribution is that between the palm of a hand and a (stiff) substrate, which can be used for instance as an identification device to identify gloves. In particular, the identification of a glove on the inner surface or also on the outer surface of the hand in a substantially 1:1 reproduction is preferred, because in this way it is easily possible to recognize one's own glove even among many that are similarly printed.

At this juncture it should once again be emphasized that a "footprint" according to one of the FIGS. 1 to 3 can very well be used as identification device not only for shoes or removable insoles, but also to identify other kinds of clothing. This is because the recognition value of such foot images is very high, and the differences between the images obtained from different people as described above are very great.

The invention claimed is:

1. An identification device worn on a body of a person, the identification device producing an image of a pressure-distribution pattern obtained by sampling pressure during contact between a body part of the person and a substantially solid object, wherein different peak pressures at different points on the substantially solid object from the contact between the body part and the substantially solid object are represented in the image by a pressure-distribution pattern arranged to correspond to the different points and having a plurality of colors, wherein the different peak pressures have associated different colors;

wherein the pressure-distribution pattern is obtained under a foot during walking on the substantially solid object and the pattern is configured to identify a shoe or a portion of a shoe worn by the person.

2. The identification device as claimed in claim 1, wherein different pressures are represented by area elements that are differently colored.

3. The identification device as claimed in claim 1, wherein the sampling of the pressure distribution comprises a plurality of samplings of various pressure distributions that occur during the contact between the body part and the substantially solid object.

4. The identification device as claimed in claim 3, wherein the pressure-distribution pattern includes at least one of mean and peak values obtained during the contact between the body part and the substantially solid object.

5. The identification device as claimed in claim 1, wherein the image is printed on an item to be worn.

6. The identification device as claimed in claim 5, wherein the image is impressed on the item by a thermotransfer process for reproducing patterns.

* * * * *